US008802028B2

(12) United States Patent
Wo et al.

(10) Patent No.: US 8,802,028 B2
(45) Date of Patent: Aug. 12, 2014

(54) DISK-BASED FLUID SAMPLE COLLECTION DEVICE

(71) Applicant: National Taiwan University, Taipei (TW)

(72) Inventors: Andrew Man Chung Wo, Taipei (TW); Chen-Lin Chen, Taipei (TW); Cheng-Wei Yang, Taipei (TW); Yu-Cheng Pan, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/930,311

(22) Filed: Jun. 28, 2013

(65) Prior Publication Data
US 2013/0287648 A1  Oct. 31, 2013

Related U.S. Application Data

(62) Division of application No. 13/104,307, filed on May 10, 2011, now Pat. No. 8,524,169.

(51) Int. Cl.
*G01N 15/06* (2006.01)
*G01N 33/00* (2006.01)
*G01N 33/48* (2006.01)

(52) U.S. Cl.
USPC ............ 422/502; 422/68.1; 422/81; 422/503; 422/504; 436/43; 436/174; 436/180

(58) Field of Classification Search
USPC ............ 422/68.1, 81, 502, 503, 504; 436/43, 436/174, 180
See application file for complete search history.

(56) References Cited

U.S. PATENT DOCUMENTS

| | | | |
|---|---|---|---|
| 7,418,977 B2 * | 9/2008 | Ducree et al. .................. | 137/825 |
| 7,776,272 B2 * | 8/2010 | Ekstrand et al. .............. | 422/506 |
| 7,863,035 B2 * | 1/2011 | Clemens et al. ........... | 435/287.1 |
| 8,323,586 B2 * | 12/2012 | Zhou et al. .................... | 422/502 |

* cited by examiner

*Primary Examiner* — Brian J Sines
(74) *Attorney, Agent, or Firm* — Rosenberg, Klein & Lee

(57) ABSTRACT

A fluid sample collection device for a disk-based fluid separation system is disclosed. The disk-based separation system includes a compact microfluidic disk with at least one flow channel pattern formed on a side surface of the disk. At least one orifice is formed on an outflow boundary of the disk and is designed in fluid communication with the flow channel pattern through a communication channel. The fluid sample collection device includes at least one collection tube having an open end serving as a fluid receiving end and corresponding to the orifice of the disk with a distance. When the disk is rotated, at least a portion of fluid sample in a sample processing reservoir formed on the disk is delivered by centripetal force through the communication channel and the orifice, and finally the expelling fluid sample is collected in the collection tube.

5 Claims, 10 Drawing Sheets

DISK-BASED FLUID SAMPLE COLLECTION DEVICE

RELATED APPLICATIONS

This application is a Divisional patent application of co-pending application Ser. No. 13/104,307, filed on 10 May 2011, now pending. The entire disclosure of the prior application, Ser. No. 13/104,307, from which an oath or declaration is supplied, is considered a part of the disclosure of the accompanying Divisional application and is hereby incorporated by reference.

FIELD OF THE INVENTION

The present invention relates to a fluid separation device, and in particular to a fluid collection device that is mounted to an outflow boundary of a microfluidic disk of a fluid separation device to collect a fluid sample that is discharged through an orifice formed in the outflow boundary of the microfluidic disk when the microfluidic disk is set in rotation.

BACKGROUND OF THE INVENTION

Techniques for fluid sample separation are of wide applications, such as separation of cells, separation of fetal cells, cell separation for whole blood samples, and separation of endothelial colony forming cells (ECFC) contained in umbilical cord blood (UCB).

For example, detection and quantification of cancer cells or rare cells present in body fluids are regarded as a potential indicator for clinical diagnoses, prognostication, and bio-medicine research. For example, circulating tumor cells (CTC) are rare in the blood of patients with metastatic cancer, and it is possible to monitor the response of CTC to adjuvant therapy. Such rear cells must be first separated from the body fluids, before detection and quantification of these rare cells can be made. For such a purpose, various cell techniques have been developed.

The cell separation techniques that are commonly used includes fluorescence activated cell separation (FACS), dielectrophoresis (DEP) cell separation, separation techniques that employ massively parallel microfabricated sieving devices, magnetically activated cell separation (MACS), and other techniques that uses optics and acoustics. Among these cell separation techniques, FACS and MACS are most often used.

Although it is often used, FACS is disadvantageous in respect of high cost, difficulty in disinfection, and consuming a great amount of sample in the operation thereof. Contrary to FACS, MACS is efficient to obtain a major quantity of target cells in a short period with a reduced consumption of sample. However, these cells must be transferred to a slide or an observation platform before they can be observed with a microscope. Such a process of transfer often leads to a great loss of cells.

Since MACS shows advantages in respect of high throughput, high performance, and simplified facility, it is often adopted in separation of fluid samples. Using immune cells to separate a desired component from a blood sample and the operation of immunofluorescence require multiple samples and manually-operated transfer, so that the result of detection is heavily dependent upon the skill of an operator, making it not fit for industrial use.

SUMMARY OF THE INVENTION

In view of the above description of the conventional techniques, it is a major issue for this field to provide a fluid sample separation technique that realizes high throughput of cell selection, easy operation, low cost, simple facility, and excellent sensitivity and reliability. Further, it is also a key issue for this field to properly collect waste fluid or desired target fluid obtained in the fluid sample separation operation.

Thus, an objective of the present invention is to provide a fluid separation and collection device, which is of low cost, is easy for collection of sample fluid, and is easy for detection and observation, for being used to collect separated target components of a fluid sample in a fluid separation operation.

The solution adopted in the present invention to achieve the above objectives is a microfluidic disk that forms therein at least one flow channel pattern. The flow channel pattern is connected by a conduction channel to an outflow boundary of the microfluidic disk to form an orifice. A fluid collection device is mounted to the outflow boundary of the microfluidic disk. The fluid collection device comprises a collection tube having a fluid receiving end, which is set to correspond to the orifice of the flow channel pattern. When the microfluidic disk is set into rotation, at least a portion of the fluid sample stored in the sample processing reservoir is acted upon by a centrifugal force induced by the rotation of the microfluidic disk to flow through the conduction channel and discharge through the orifice to be received by the fluid receiving of the collection tube and collected in the collection tube. A sealing cover is operable through hand rotation or electrically-driven rotation to have an air passage of the sealing cover to align or close an air vent of a selected sample storage reservoir. Alternatively, the air passage of the sealing cover is replaced by a solenoid-controlled air passage structure.

In a preferred embodiment of the present invention, at least one magnetic unit is set on a top of the sealing cover at a location corresponding to the sample processing reservoir of the microfluidic disk for providing a uniform magnetic force of predetermined magnitude on the sample processing reservoir to improve fluid collection.

BRIEF DESCRIPTION OF THE DRAWINGS

The present invention will be apparent to those skilled in the art by reading the following description of preferred embodiments thereof, with reference to the attached drawings, in which.

DETAILED DESCRIPTION OF THE PREFERRED EMBODIMENTS

Figure 1:
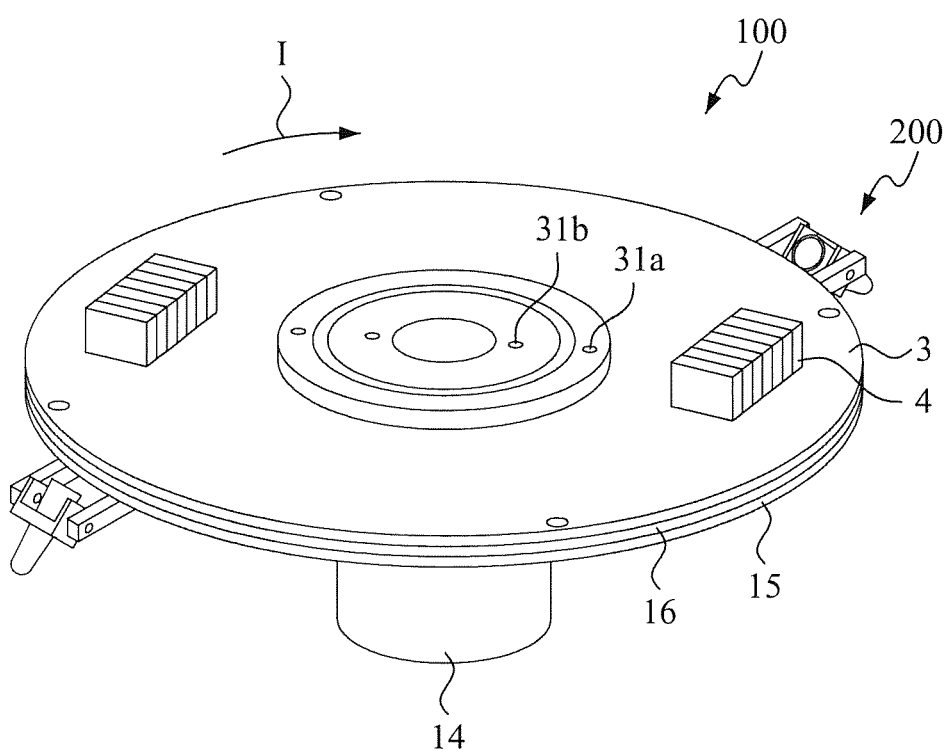
FIG. 1 is a perspective view showing a preferred embodiment of the present invention.
Figure 2:
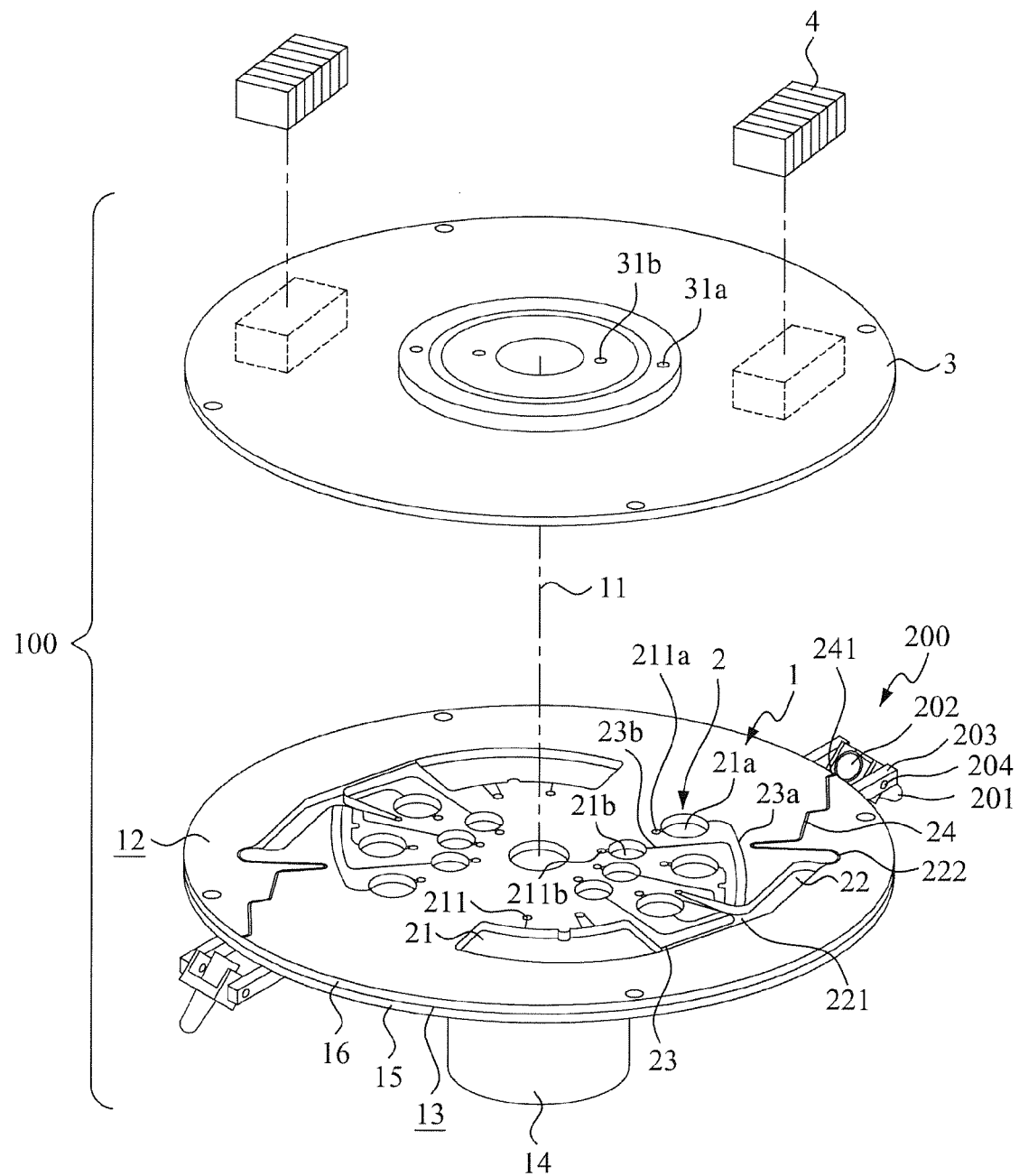
FIG. 2 is an exploded view showing the preferred embodiment of the present invention.

With reference to the drawings and in particular to FIG. 1, which is a perspective view showing a preferred embodiment of the present invention, and FIG. 2, which is an exploded view showing a microfluidic disk according to the preferred embodiment of the present invention, the present invention provides a disk-based fluid sample separation system, generally designated at 100, which comprises a microfluidic disk 1 having a geometric center 11, a top surface 12, and a circumferential surface 13, which serves as an outflow boundary of the disk. The geometric center 11 is coupled to a spindle of a rotation driving device 14, whereby the microfluidic disk 1 is selectively driven by the rotation driving device 14 to rotate about the geometric center 11, which serves as a rotation center, in a predetermined rotation direction I.

The microfluidic disk 1 forms a flow channel pattern 2. In the instant embodiment, the microfluidic disk 1 is composed of a bottom base board 15 and a flow channel pattern layer 16 formed on the bottom base board 15. The flow channel pattern 2 is defined in and by the flow channel pattern layer 16. The microfluidic disk 1 is covered by a sealing cover 3 set on the top surface 12 thereof.

Figure 3:
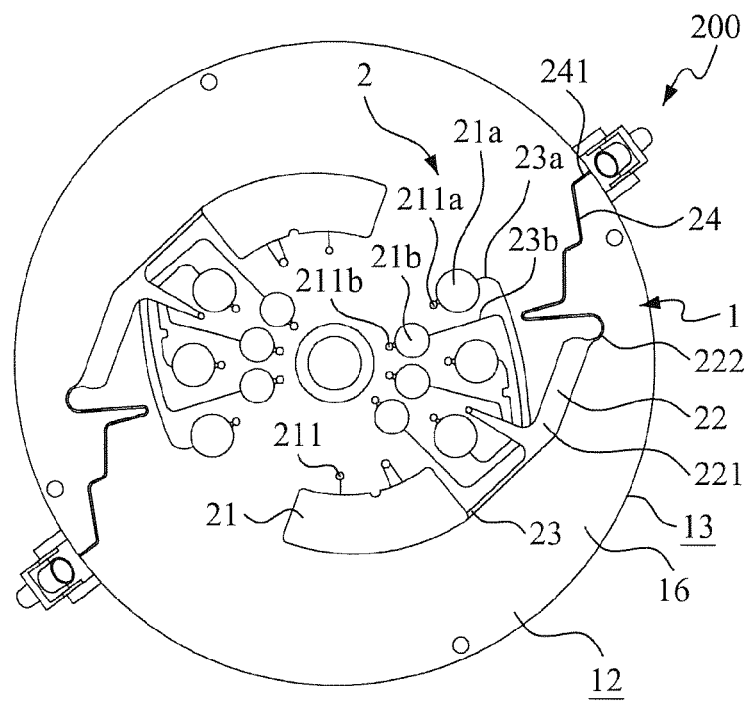
FIG. 3 is a top plan view showing a microfluidic disk of the preferred embodiment of the present invention.

Referring also to FIG. 3, which is a top plan view of the microfluidic disk 1 shown in FIG. 2, the flow channel pattern 2 comprises at least one sample storage reservoir 21, which is formed in the flow channel pattern layer 16 of the microfluidic disk 1 to store a fluid sample (such as a blood sample). The sample storage reservoir 21 is in fluid communication with at least one air vent 211. The flow channel pattern 2 also comprises at least one secondary sample storage reservoir 21*a*, which is formed in the flow channel pattern layer 16 of the microfluidic disk 1 to store a secondary sample (such as reaction reagent). Each secondary sample storage reservoir 21*a* is in fluid communication with a respective air vent 211*a*.

In an embodiment, a plurality of secondary sample storage reservoirs 21*a* that each comprises an air vent 211*a* may be arranged on the microfluidic disk 1 as a circle centered at the geometric center 11. Alternatively, secondary sample storage reservoirs comprising air vents may be arranged along inner and outer concentric circles on the microfluidic disk 1. As shown in the drawing, a plurality of secondary sample storage reservoirs 21*a* that each comprises an air vent 211*a* is arranged as an outer circle in the flow channel pattern layer 16 of the microfluidic disk 1, and a plurality of secondary sample storage reservoirs 21*b* that each comprises an air vent 211*b* is arranged as an inner, concentric circle in the flow channel pattern layer 16 of the microfluidic disk 1.

The flow channel pattern 2 further comprises at least one sample processing reservoir 22. The sample processing reservoir 22 is located closer to the outflow boundary 13 of the microfluidic disk 1 than the sample storage reservoir 21 is. The sample processing reservoir 22 has a fluid inlet end 221 and a fluid outlet end 222. The fluid inlet end 221 communicates through at least one communication channel 23, 23*a* with the sample storage reservoir 21 and the secondary sample storage reservoir(s) 21*a*. The fluid outlet end 222 communicates with a conduction channel 24. The conduction channel 24 has an opposite end extending to the outflow boundary 13 of the microfluidic disk 1 to form an orifice 241.

Figure 4:
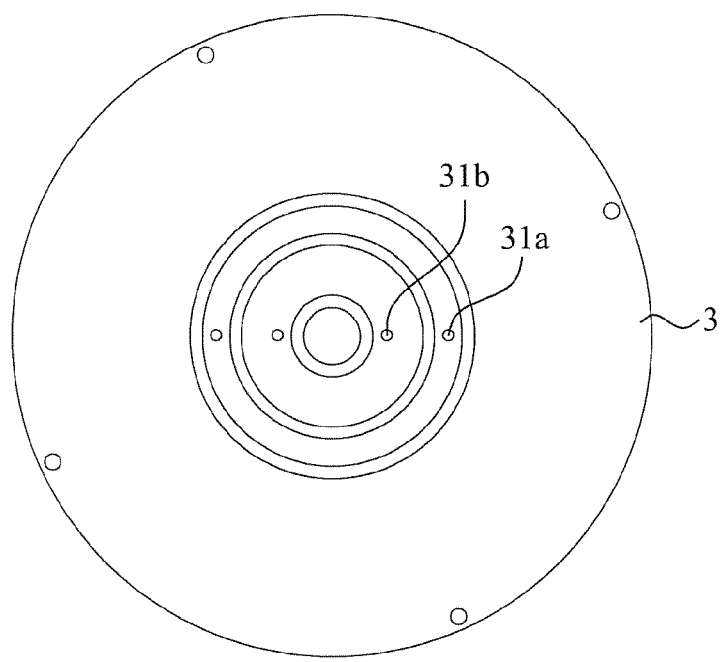
FIG. 4 is a top plan view showing a sealing cover of the preferred embodiment of the present invention.
Figure 5:
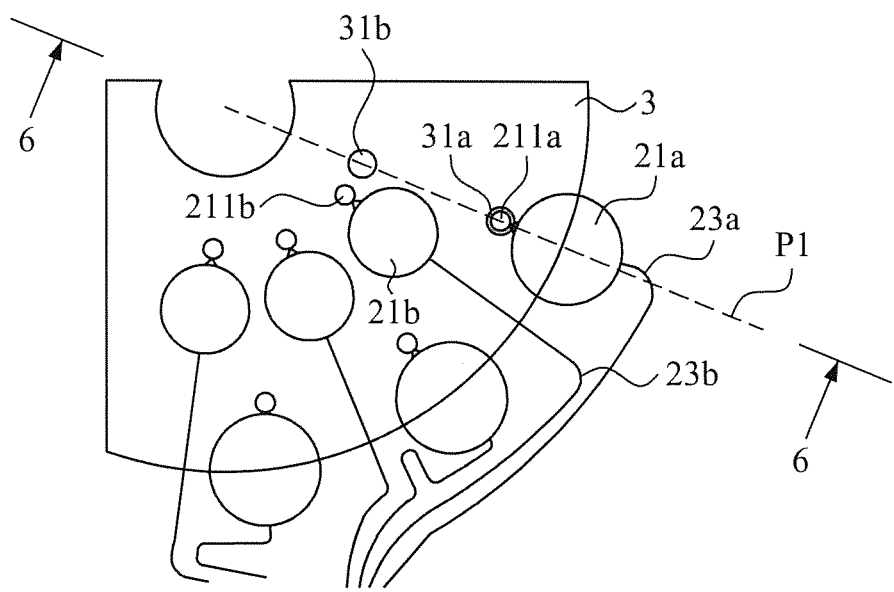
FIG. 5 is a schematic view showing an air passage of the sealing cover of the present invention in alignment with an air vent of a sample storage reservoir to set the air vent in an open condition.
Figure 6:
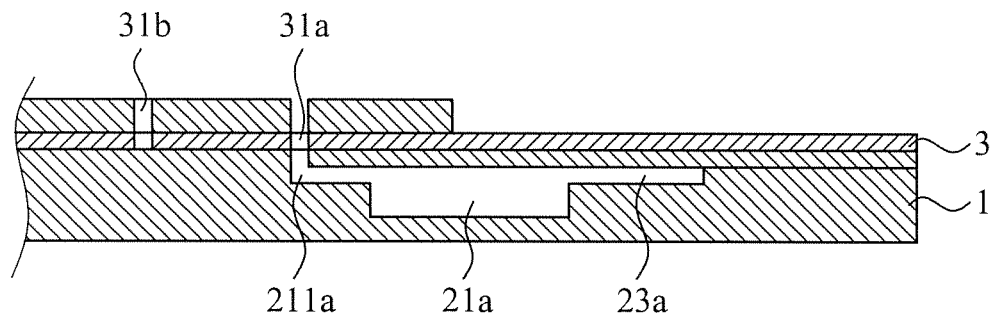
FIG. 6 is a cross-sectional view showing the sealing cover of FIG. 5 in a first position.

The sealing cover 3 is positioned on the top surface of the microfluidic disk 1 and forms at least one air passage 31*a*, 31*b* (also see FIGS. 2 and 4). The sealing cover 3 is rotatable with respect to the microfluidic disk 1. For example, when the sealing cover 3 is rotated to a first angular position P1 (also see FIG. 5, as well as the cross-sectional view of FIG. 6), the air passage 31*a* of the sealing cover 3 is located exactly in alignment with the air vent 211*a* of the sample storage reservoir 21*a*, thereby setting the air vent 211*a* in an open condition, while the air vents of the remaining sample storage reservoir are kept in a closed condition. Under this condition, when the microfluidic disk 1 is driven to rotate about the geometric center 11, and the air passage (such as 31*a*) of the sealing cover 3 is in alignment with the air vent (such as 211*a*) of a selected sample storage reservoir (such as 21*a*), the fluid sample stored in the selected sample storage reservoir 21*a* may be driven by a centrifugal force to flow through the communication channel 23*a* into the sample processing reservoir 22.

Figure 7:
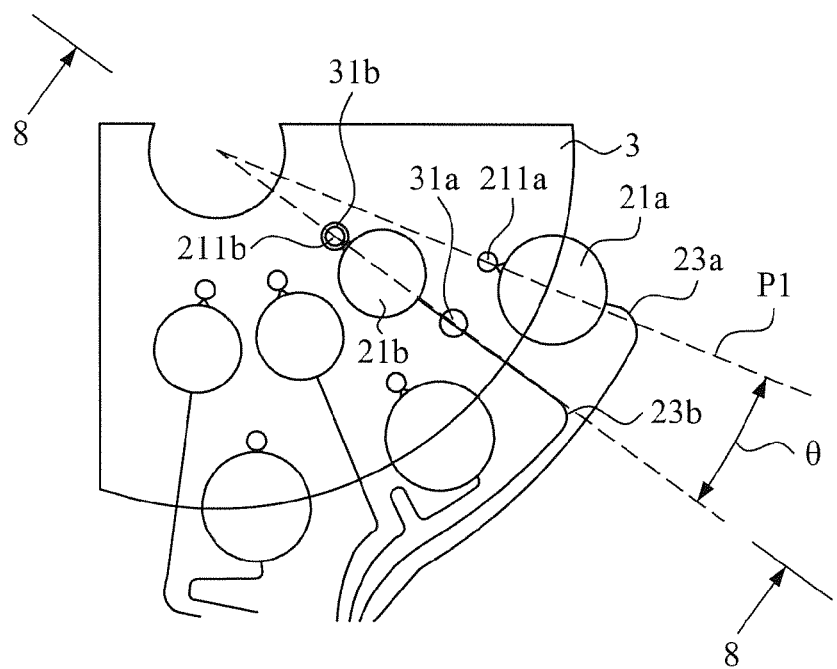
FIG. 7 is a schematic view showing the sealing cover of the present invention being rotated by an angle to have the air passage aligning an air vent of another sample storage reservoir to set the air vent in an open condition.
Figure 8:
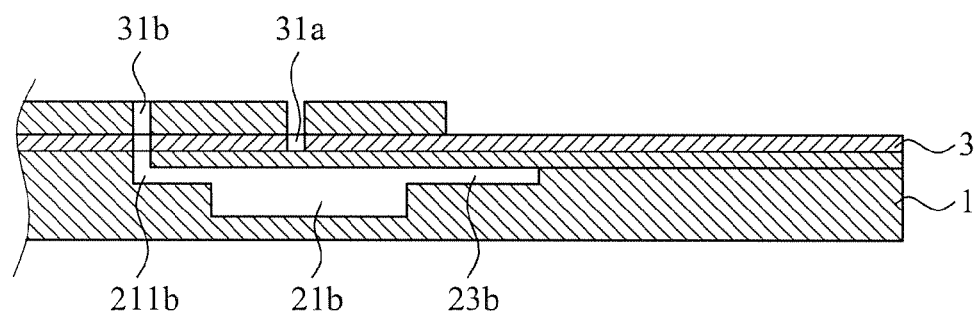
FIG. 8 is a cross-sectional view showing the sealing cover of FIG. 7 in a second position.

When the sealing cover 3 is rotated by a predetermined angle θ (also see FIG. 7, as well as the cross-sectional view of FIG. 8), the air passage 31*b* of the sealing cover 3 is positioned to align the air vent 211*b* of the sample storage reservoir 21*b*, thereby setting the air vent 211*b* in an open condition, while the air vents of the remaining sample storage reservoirs are kept closed. The number of the air passages formed in the sealing cover 3 may be varied as desired, and the locations where the air passages are formed are also variable as desired. Through the selective rotation of the sealing cover 3, it is possible to selectively set the air vent of each individual sample storage reservoir in an open condition or a closed condition.

Figure 9:
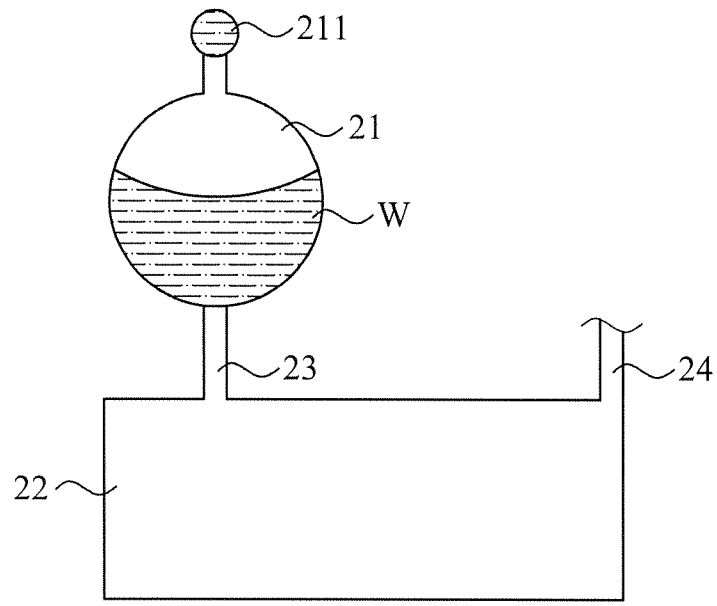
FIG. 9 is a schematic view showing the air vent of the sample storage reservoir of the present invention in a closed condition, whereby a fluid sample contained in the sample storage reservoir is not allowed to flow to a sample processing reservoir.
Figure 10:
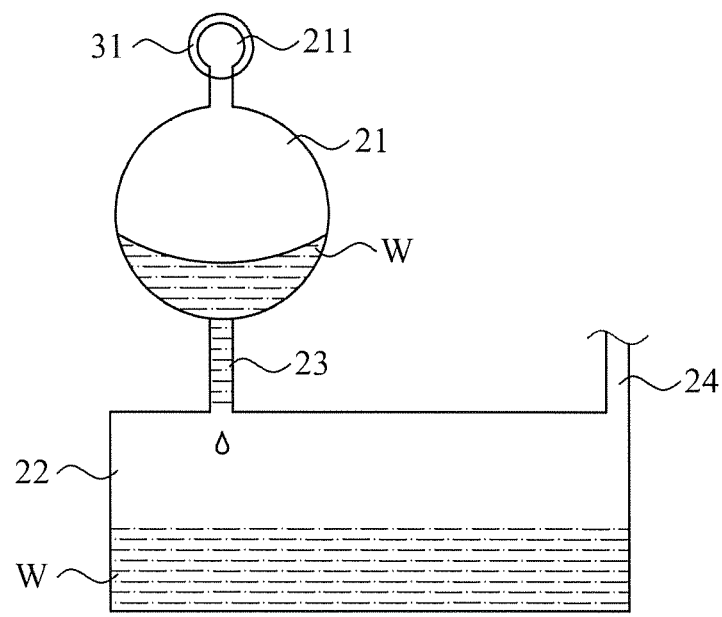
FIG. 10 is a schematic view showing the air vent of the sample storage reservoir of the present invention in an open condition, whereby a fluid sample contained in the sample storage reservoir is acted upon by a centrifugal force to flow through a communication channel to the sample processing reservoir.

Taking the sample storage reservoir 21 as an example, when the air vent 211 of the sample storage reservoir 21 is set in a closed condition (see FIG. 9), a fluid sample W contained in the sample storage reservoir 21 is not allowed to flow to the sample processing reservoir 22, whether the microfluidic disk 1 is kept standstill (not in rotation) or the microfluidic disk 1 is in rotation. On the other hand, when the air vent 211 of the sample storage reservoir 21 is in an open condition (see FIG. 10), if the microfluidic disk 1 is kept standstill (not in rotation), the fluid sample W contained the sample storage reservoir 21 cannot flow to the sample processing reservoir 22, but if the microfluidic disk 1 is driven and rotated, the fluid sample W contained in the sample storage reservoir 21 is acted upon by a centrifugal force to flow into the sample processing reservoir 22.

With such an operation model, for an arrangement of a plurality of sample storage reservoirs, the angular displacement θ of the sealing cover 3 can be selected through rotation of the cover (see FIG. 7) in order to selectively set the air vents of some of the sample storage reservoirs in a closed condition, while the air vents of the selected sample storage reservoirs are simultaneously opened to allow the fluid samples contained in the selected sample storage reservoirs to flow into the sample processing reservoir. Repeating the rotating and positioning process for the sealing cover 3 would allow the fluid sample contained in each of the sample storage reservoirs to be conducted into the sample processing reservoir.

Figure 11:
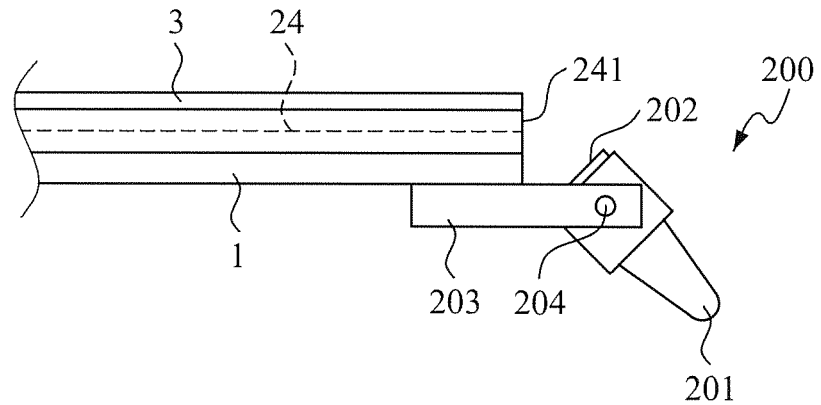
FIG. 11 is a schematic view showing a liquid collection device arranged at an outflow boundary of the microfluidic disk according to the present invention.
Figure 12:
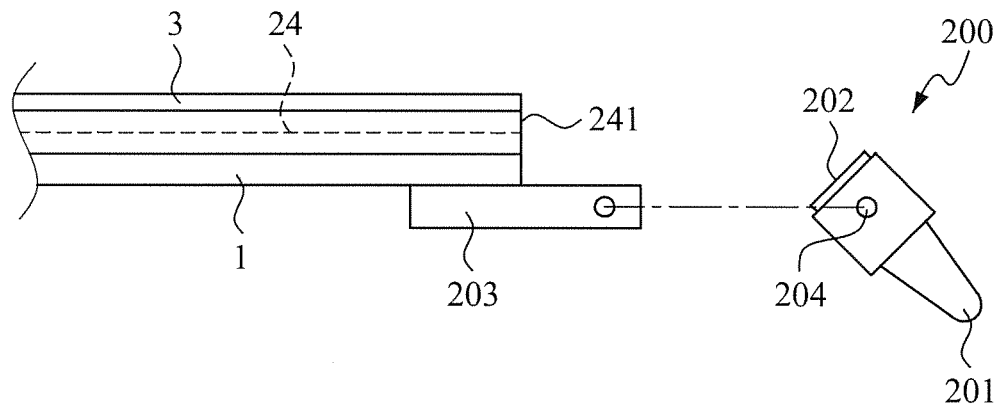
FIG. 12 is a schematic exploded view showing the liquid collection device arranged at the outflow boundary of the microfluidic disk according to the present invention.

The disk-based fluid separation system 100 according to the present invention further comprises a fluid sample collection device 200 (see FIGS. 1, 2, and 3), which is arranged adjacent to the outflow boundary 13 of the microfluidic disk 1 and corresponds to the orifice 241 of the conduction channel 24. Also referring to FIGS. 11 and 12, the fluid sample collection device 200 comprises a collection tube 201, which has an open end serving as a fluid receiving end 202. The collection tube 201 is set at the outflow boundary 13 of the microfluidic disk 1 with the fluid receiving end 202 of the collection tube 201 opposing the orifice 241 of the conduction channel 24 defined in the flow channel pattern 2. A bracket 203 is mounted to a bottom side of the microfluidic disk 1 under the outflow boundary 13. The bracket 203 has an outer end that is coupled to the collection tube 201 with a pivot pin 204 in order to position the collection tube 201 adjacent to the outflow boundary 13 of the microfluidic disk 1.

When the microfluidic disk 1 is driven and rotated, with at least one air vent in communication with the sample processing reservoir 22 in an open condition, at least a portion of the fluid sample contained in the sample processing reservoir 22 is acted upon by a centrifugal force induced by the rotation of the microfluidic disk 1 to flow through the conduction channel 24 and the discharge through the orifice 241 to thereby be received by the fluid receiving end 202 of the collection tube 201 and collected in the connection tube 201.

Figure 13:
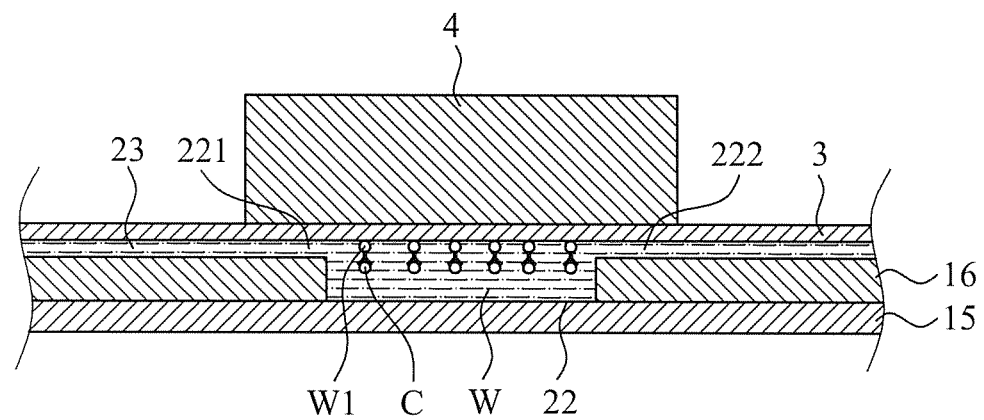
FIG. 13 is a cross-sectional view showing a magnetic unit arranged on a top of a sealing cover according to the present invention.
Figure 14:
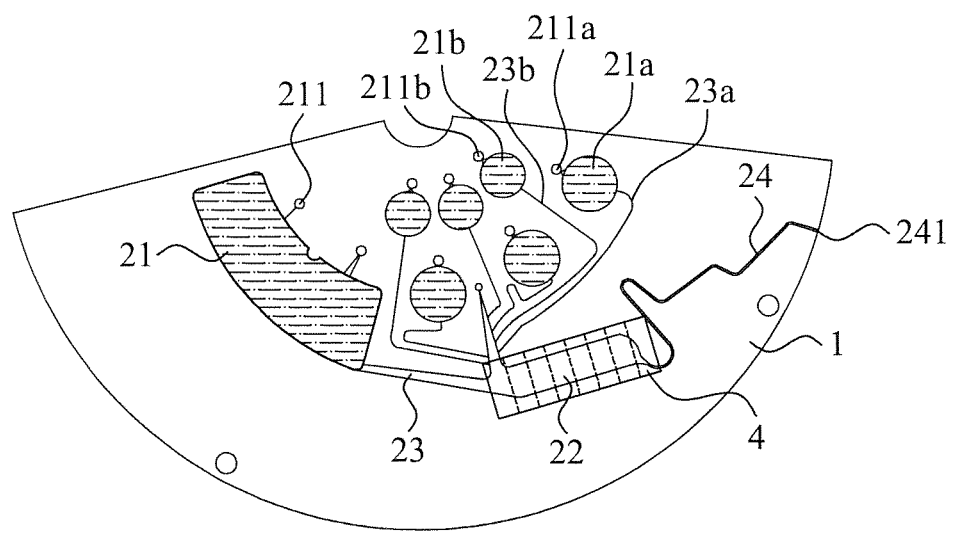
FIGS. 14-18 are schematic views demonstrating a fluid sample contained in the sample storage reservoir according to the present invention and secondary samples contained in secondary sample storage reservoirs conducted, under the control of air vents and subjected to rotating motion, to the sample processing reservoir.
Figure 15:
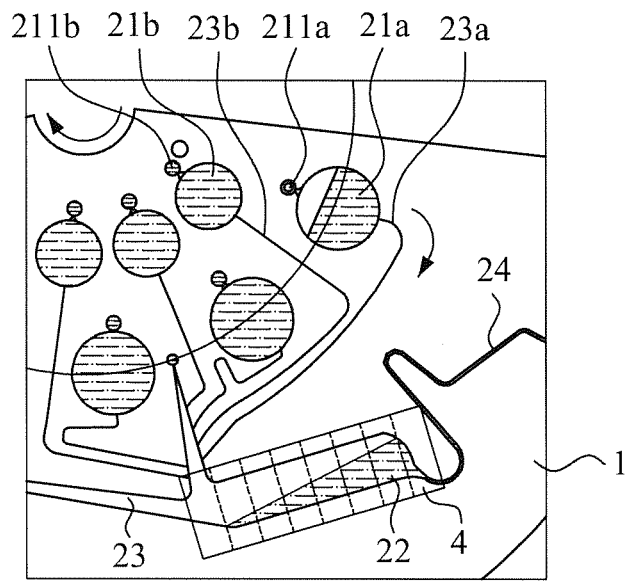
Figure 16:
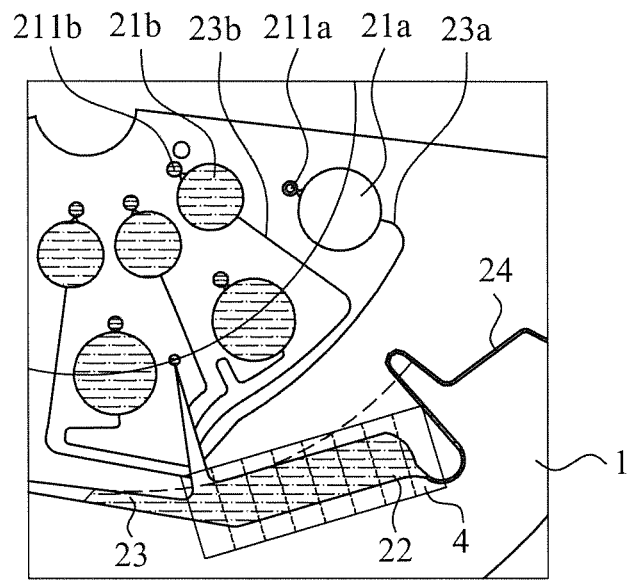

Also referring to FIG. 13, at least one magnetic unit 4 is additionally provided on the top of the sealing cover 3 at a location corresponding to the sample processing reservoir 22 of the microfluidic disk 1 for providing a predetermined magnetic field above the sample processing reservoir 22 of the microfluidic disk 1.

In an example application, the present invention is applied to separation of cells that are labeled with immunomagnetic beads. A fluid sample W with which the operation of cell separation is to be performed is first filled into the sample storage reservoir 21. The fluid sample W contains two types of cell, one of which (target samples W1) is labeled with immunomagnetic beads C. With the sealing cover 3 being angularly displaced to have the air passage 31a aligning the air vent 211 of the sample storage reservoir 21 and thus opening the air vent 211, when the microfluidic disk 1 is driven by the rotation driving device 14 to rotate in a predetermined rotation direction I, the fluid sample W is acted upon by the centrifugal force induced by the rotation of the microfluidic disk 1 and thus flows from the sample storage reservoir 21 through the communication channel 23 into the sample processing reservoir 22. Under this condition, the target samples W1 that are labeled with immunomagnetic beads C contained in the fluid sample W are subjected to magnetic attraction induced by the magnetic field of the magnetic unit 4 to collect at the underside of the sealing cover 3. In the embodiment illustrated, the magnetic unit 3 comprises a rectangular array of magnets, which applies a uniform magnetic field of a predetermined intensity on the sample processing reservoir 22 of the microfluidic disk 1.

In another example of application, the present invention is used to separate for example MCF7 cells and Jurkat cells. It is apparent that the present invention is applicable to separation of fetal cells, separation of cells from whole blood sample, and separation of endothelial colony forming cells (ECFC) contained in umbilical cord blood (UCB).

FIGS. 14-18 are schematic views demonstrating a fluid sample contained in the sample storage reservoir according to the present invention and secondary samples contained in secondary sample storage reservoirs conducted, under the control of air vents and being subjected to a rotating motion, to the sample processing reservoir. Firstly, the fluid sample is filled into the sample storage reservoir 21 and secondary samples are respectively filled into the respective secondary sample storage reservoirs 21a, 21b (see FIG. 12). The sealing cover 3 is then rotated to have the air passage 31b of the sealing cover 3 aligning the air vent 211a of the sample storage reservoir 21a. Afterwards, when the microfluidic disk 1 is put into rotation, the secondary sample contained in the secondary sample storage reservoir 21a is acted upon by a centrifugal force to flow through the communication channel 23a into the sample processing reservoir 22 (see FIG. 15).

Figure 17:
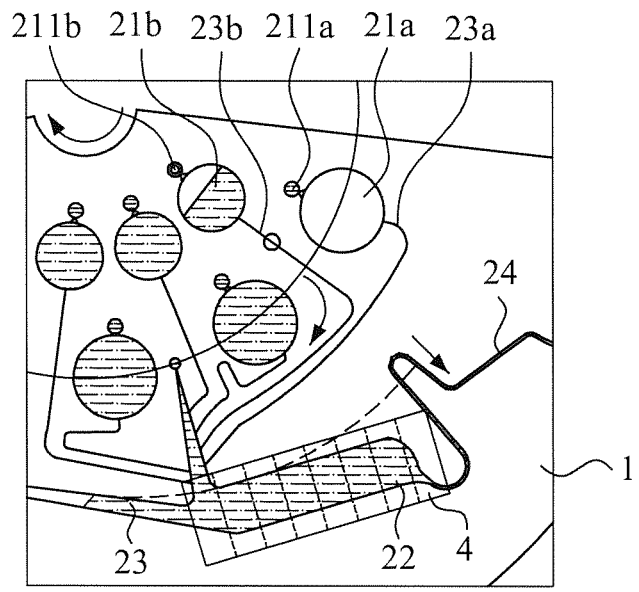
Figure 18:
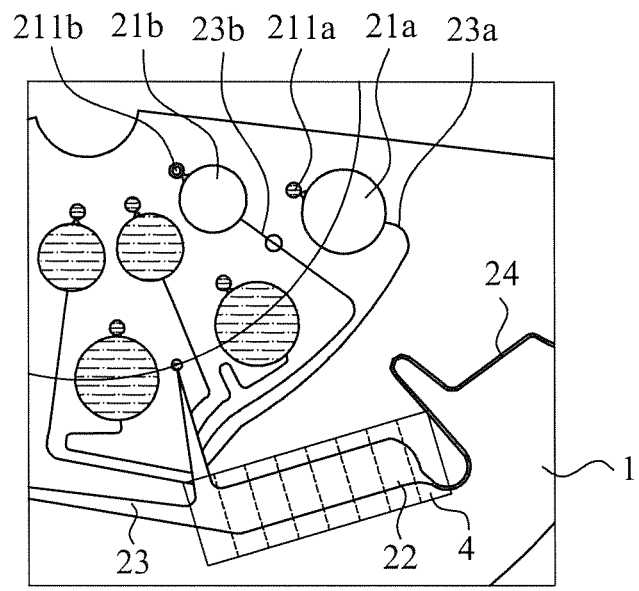

After the secondary sample of the secondary sample storage reservoir 21a is completely received into the sample processing reservoir 22 (see FIG. 16), the sealing cover 3 may be rotated again to have the air passage 31a of the sealing cover 3 aligning the air vent 211b of the sample storage reservoir 21b (see FIG. 17). Under this condition, when the microfluidic disk 1 is put into rotation, the secondary sample contained in the secondary sample storage reservoir 21b is acted upon by a centrifugal force to flow through the communication channel 23b into the sample processing reservoir 22 (see FIG. 18). As such, through sequential rotation of the sealing cover 3, the fluid sample contained in the sample storage reservoir 22 and the secondary samples contained in the secondary sample storage reservoirs 21a, 21b can be individually conducted into the sample processing reservoir 22.

In the previously discussed embodiment, the sealing cover 3 is positioned on the microfluidic disk 1 and is rotatable by an operator's hands so as to have the air passage of the sealing cover 3 to correspond to or close an air vent of a selected sample storage reservoir. In another embodiment of the present invention, hand rotating of the sealing cover 3 is substituted by motor-driven rotation. Further, the air vent of the sealing cover 3 may be replaced by a solenoid controlled air vent structure.

Although the present invention has been described with reference to the preferred embodiment thereof, it is apparent to those skilled in the art that a variety of modifications and changes may be made without departing from the scope of the present invention which is intended to be defined by the appended claims.

What is claimed is:

1. A disk-based fluid collection device, comprising:
   a microfluidic disk, which has a geometric center, a top surface, and an outflow boundary;
   a flow channel pattern, which is formed in the microfluidic disk, the flow channel pattern comprising at least one air vent, at least one conduction channel, which extends to the outflow boundary of the microfluidic disk to form an orifice, and at least one sample storage reservoir, which is formed in the microfluidic disk to store a selected fluid sample, the sample storage reservoir is in fluid communication with at least one air vent, the sample storage being in communication with a sample processing reservoir through a communication channel; and a fluid connection device, which comprises a collection tube having an open fluid receiving end, the collection tube being positioned at the outflow boundary of the microfluidic disk with the fluid receiving of the collection tube opposing the orifice of the flow channel pattern;

whereby when the microfluidic disk is set into rotation and the air vent is in an open condition, at least a portion of the fluid sample stored in the sample processing reservoir is acted upon by a centrifugal force induced by the rotation of the microfluidic disk to flow through the conduction channel and discharge through the orifice to be received by the fluid receiving of the collection tube and collected in the collection tube.

2. The disk-based fluid sample collection device as claimed in claim 1, wherein the flow channel pattern comprises at least one secondary sample storage reservoir, which is formed in the microfluidic disk for storing a secondary sample, the secondary sample storage reservoir being in communication with at least one air vent and being connected by a communication channel to the sample processing reservoir.

3. The disk-based fluid sample collection device as claimed in claim 1, wherein the microfluidic disk comprises a bottom base board and at least one flow channel pattern layer, the flow channel pattern being formed in the flow channel pattern layer.

4. The disk-based fluid sample collection device as claimed in claim 1, wherein a sealing cover is set to cover the top surface of the microfluidic disk and at least one magnetic unit is set at a location corresponding to the sample processing reservoir of the microfluidic disk.

5. The disk-based fluid sample collection device as claimed in claim 1, wherein the fluid collection device comprises a bracket, which is mounted to the outflow boundary of the microfluidic disk and has an outer end coupled to the collection tube to position the collection tube at the outflow boundary of the microfluidic disk.

* * * * *